United States Patent [19]

Maurer

[11] Patent Number: 4,849,519
[45] Date of Patent: Jul. 18, 1989

[54] PREPARATION OF 6-HYDROXY-3-PYRIDINECARBOXYLIC ACID ESTERS

[75] Inventor: Fritz Maurer, Wuppertal, Fed. Rep. of Germany

[73] Assignee: Bayer Aktiengesellschaft, Leverkusen, Fed. Rep. of Germany

[21] Appl. No.: 118,364

[22] Filed: Nov. 6, 1987

[30] Foreign Application Priority Data

Nov. 27, 1986 [DE] Fed. Rep. of Germany ....... 3640583

[51] Int. Cl.$^4$ .................... C07D 213/64; C07D 213/55
[52] U.S. Cl. ..................................... 546/298; 560/171
[58] Field of Search ......................................... 546/298

[56] References Cited

FOREIGN PATENT DOCUMENTS 0867930 8/1959 United Kingdom .

OTHER PUBLICATIONS

Methoden der Organischen Chemie (Houben-Weyl), vol. VIII (Sauerstoff-Verbindungen III), 1952, pp. 658-660.
Organic Syntheses, Coll. vol. I (1941), pp. 153, 154, 179, 180 (Carson, Scott and Vose).
Ber. 17, 2384 (1884), H. von Pechmann und W. Welsh.
Caldwell et al, J. Am. Chem. Soc. 66, 1482 (1944).
Anghelide et al, Tetrahedron, pp. 623-632-vol. 30 (1974).
Ruzicka, Helv. Chim. Acta, vol. 4, pp. 482-485 (1921).
Chemical Abstracts, Band 81, No. 13, 30 Sep. 1974, Columbus, Ohio, U.S.A., entry 77429b.

Primary Examiner—John M. Ford
Attorney, Agent, or Firm—Sprung Horn Kramer & Woods

[57] ABSTRACT

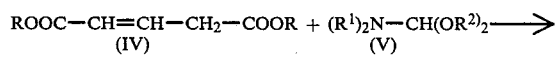
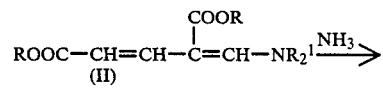
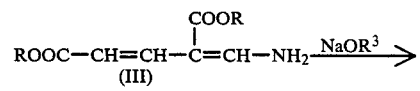
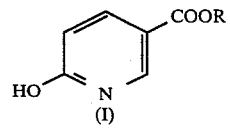

R, $R^1$, $R^2$ and $R^3$ are alkyl.

II and III are new and I is a known intermediate for insecticides.

8 Claims, No Drawings

PREPARATION OF 6-HYDROXY-3-PYRIDINECARBOXYLIC ACID ESTERS

The present invention relates to a new process for the preparation of 6-hydroxy-3-pyridinecarboxylic acid esters, intermediate products which can be used for carrying out the process, and processes for the preparation of such intermediate products. The process products are known and can be used as intermediate products for the preparation of insecticides.

It is already known that 6-hydroxy-3-pyridine-carboxylic acid esters can be obtained by heating hydroxysuccinic acid esters with fuming sulphuric acid and reacting the resulting coumalic acid derivatives with ammonia. The disadvantage of this reaction is the use of relatively large amounts of fuming sulphuric acid, which must be removed from the reaction mixture again during working up and is not easy to handle ecologically (compare Ber. 17, 2384 (1884), Helv. Chim. Acta, 4 482 (1921) and J. Am. Chem. Soc. 66, 1482 (1944)).

It is furthermore known that the 6-hydroxy-3-pyridinecarboxylic acid esters and the corresponding tautomeric α-pyridonecarboxylic acid esters can be prepared by reacting enamine derivatives with aprotic polar diluents at temperatures between 160° C. and 190° C. The disadvantage of this process is the relatively high reaction temperature and the high energy consumption thereby caused (compare Tetrahedron, pages 623-632, (1974)).

It has now been found that 6-hydroxy-3-pyridinecarboxylic acid esters of the general formula (I)

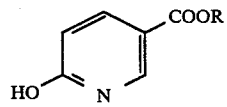  (I)

in which R represents alkyl, are obtained by a process in which 1-dialkylamino-1,3-butadiene-2,4-dicarboxylic acid esters of the formula (II)

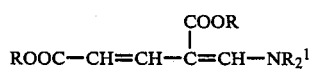  (II)

in which
R has the abovementioned meaning and
R$^1$ represents alkyl, (a) are reacted with gaseous ammonia in the presence of alkali metal alcoholates and in the presence of diluents at temperatures between 0° C. and 120° C., or (b) in a two-stage reaction, are reacted with gaseous ammonia and in the presence of diluents at temperatures between 0° C. and 50° C. to give the amino derivatives of the formula (III)

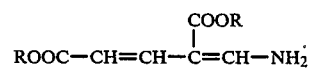  (III)

in which R has the abovementioned meaning, if appropriate the resulting compounds of the formula (III) are isolated, and the amino derivatives of the formula (III) are then reacted in a 2nd reaction stage with alkali metal alcoholates and in the presence of diluents at temperatures between 0° C. and 120° C. to give the compounds (I).

Surprisingly, the compounds of the formula (I) can be prepared in good yields in a simple manner and starting from inexpensive new intermediate products with the aid of the process according to the invention (variants (a) and (b)).

The compounds of the formula (I) in which R represents $C_1$-$C_6$-alkyl are preferably prepared with the aid of the process according to the invention.

The compounds of the formula (I) in which R represents $C_1$-$C_4$-alkyl, are particularly preferably prepared with the aid of the process according to the invention.

The compounds of the formula (I) are preferably prepared by process variant (a) ("one-pot process").

If diethyl 1-dimethylamino-1,3-butadiene-2,4-dicarboxylate, ammonia and sodium ethylate are used as starting substances for the process according to the invention in variant (a), the reaction can be outlined y the following equation:

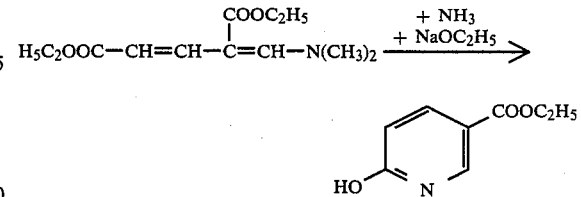

If diethyl 1-dimethylamino-1,3-butadiene-2,4-dicarboxylate and ammonia are used as starting substances for the process according to the invention in variant (b), the diethyl 1-amino-1,3-butadiene-2,4-dicarboxylate formed is isolated and this ester is reacted further with sodium ethylate, the reaction sequence can be outlined by the following equation:

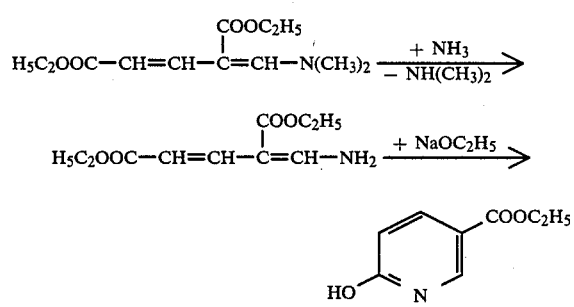

Formula (II) provides a general definition of the 1-dialkylamino-1,3-butadiene-2,4-dicarboxylic acid esters to be used as starting substances for the inventive process (variants (a) and (b)). In this formula, R preferably represents those radicals which have been mentioned above as preferred or as particularly preferred in the context of the substituent definition for formula (I). R$^1$ in this formula preferably represents $C_1$-$C_6$-alkyl. R$^1$ particularly preferably represents $C_1$-$C_4$-alkyl.

The compounds of the formula (II) are new and are part of the present invention. They can be prepared in a simple manner by a process in which, for example, glutaconic acid esters of the formula (IV)

  (IV)

in which R has the abovementioned meaning, are reacted with N,N-dialkylformamide acetals of the formula (V)

$$(R^1)_2N-CH(OR^2)_2 \qquad (V)$$

in which
$R^1$ has the abovementioned meaning and
$R^2$ represents alkyl,
if appropriate in the presence of acid anhydrides, such as, for example, acetic anhydride, and if appropriate in the presence of inert diluents, such as, for example, toluene, at temperatures between 0° C. and 40° C.

Formula (IV) provides a general definition of the glutaconic acid esters to be used as starting compounds. In this formula, R preferably represents those radicals which have been mentioned above as preferred or as particularly preferred in the context of the substituent definition for formula (I).

The glutaconic acid esters of the formula (IV) are known compounds of organic chemistry.

Examples which may be mentioned of the compounds of the formula (IV) are: dimethyl, diethyl, di-n-propyl, di-i-propyl and di-n-butyl glutaconate.

Formula (V) provides a general definition of the N,N-dialkylformamide acetals furthermore to be used as starting substances for the preparation of the new compounds of the formula (II). In this formula (V), $R^1$ and $R^2$ preferably represent $C_1-C_6$-alkyl and particularly preferably represent $C_1-C_4$-alkyl.

The N,N-dialkylformamide acetals of the formula (V) are generally known compounds of organic chemistry.

Examples which may be mentioned of the compounds of the formula (V) are: N,N-dimethylformamide dimethyl acetal, N,N-dimethylformamide diethyl acetal, N,N-dimethylformamide di-n-propyl acetal, N,N-dimethylformamide di-i-propyl acetal and N,N-dimethylformamide di-n-butyl acetal. N,N-Dimethylformamide dimethyl acetal is preferably used as the reaction component for the preparation of the new compounds.

Formula (III) provides a general definition of the amino derivatives to be used as starting substances for the inventive process (variant (b)/2nd stage). In this formula, R preferably represents those radicals which have been mentioned above as preferred or as particularly preferred in the context of the substituent definition for formula (I).

The compounds of the formula (III) are new and are part of the present invention. They can be prepared in a simple manner by the inventive process (variant (b), 1st stage).

Examples which may be mentioned of the amino derivatives of the formula (III) are: dimethyl, diethyl, di-n-propyl, di-i-propyl and di-butyl 1-amino-1,3-butadiene-2,4-dicarboxylate.

The inventive process for the preparation of the compounds of the formula (I) is preferably carried out using inert organic solvents. Preferred possible diluents here for variant (a) are aromatic hydrocarbons, such as xylene, toluene and benzene.

Preferred possible diluents for the 1st and 2nd stage of process variant (b) are lower alcohols, such as methanol, ethanol, n-propanol, i-propanol, n-butanol, i-butanol, sec.-butanol and tert.-butanol.

Preferred possible alkali metal alcoholates for process variants (a) and ((b)/stage 2) are sodium and potassium methylate and ethylate and potassium tert.-butylate.

Sodium methylate and ethylate are particularly preferably used.

The reaction temperatures can be varied within a substantial range in the process according to the invention (variants (a) and (b)). The reaction is in general carried out in process variants (a) and ((b)/stage 2) at temperatures between 0° C. and 120° C., preferably at temperatures between 20° C. and 100° C.; and in process variant ((b)/stage 1) at temperatures between 0° C. and 50° C., preferably at temperatures between 10° C. and 35° C. The process according to the invention is preferably carried out under normal pressure.

For carrying out the process according to the invention (variant (a)), 1 to 1.5 mols, preferably 1 to 1.3 mols of alkali metal alcoholate and 2 to 10 mols, preferably 3 to 6 mol of gaseous ammonia are employed per mol of the compound of the formula (II). In general, a procedure is followed in which ammonia is passed to saturation into a solution of alcoholate and alcohol. The compound of the formula (II) is then added to the solution and the mixture is stirred at the required temperature for several hours. To liberate the compound of the formula (I), concentrated hydrochloric acid is added so that a pH value of 4 is reached. Further working up is effected by customary methods.

For carrying out the process according to the invention variant (b)), in the 1st stage 2 to 10 mols. preferably 3 to 6 mols of gaseous ammonia are employed per mol of the compound of the formula (II). In general, a procedure is followed in which ammonia is passed into the alcohol, the required amount of the compound of the formula (II) is added to this mixture and the mixture is stirred at the required temperature for several hours. After any working up and isolation of the compound of the formula (III) which may be carried out, a procedure is followed in the 2nd stage in which 1 mol of the compound of the formula (III) is stirred in the presence of alcohol and 1 to 1.5 mols, preferably 1 to 1.3 mols, of alcoholate at the required temperature for several hours. To liberate the compound of the formula (I), concentrated hydrochloric acid is added so that a pH value of 4 is reached. Working up is effected by customary methods.

The 6-hydroxy-3-pyridinecarboxylic acid esters of the formula (I) to be prepared by the inventive process can be used as intermediate products for the preparation of nitromethylene derivatives which have an action as insecticides (compare European Patent No. A-163,855 and European Patent No. A-192,060).

Further processing of the compounds of the formula (I) to known insecticides may be illustrated with the aid of the following equation by way of example:

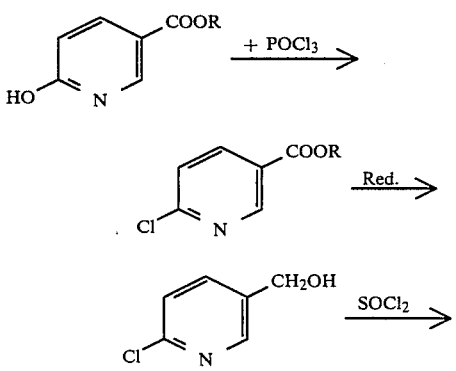

-continued

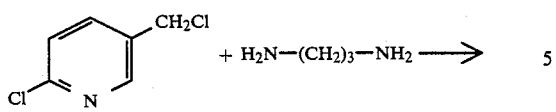
+ H₂N—(CH₂)₃—NH₂ →

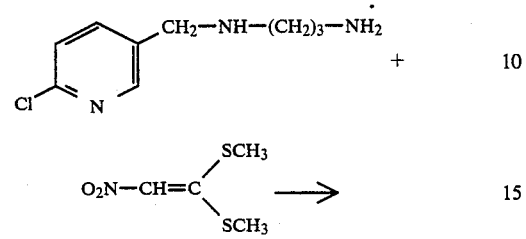
+

O₂N—CH=C(SCH₃)(SCH₃) →

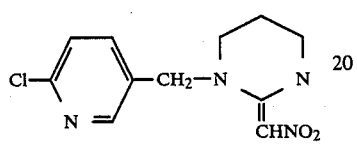

Preparation Examples
EXAMPLE 1

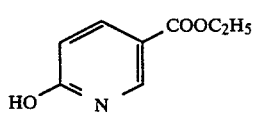

(Process variant (a))

6 g (0.025 mol) of diethyl 1-dimethylamino-1,3-butadiene-2,4-dicarboxylate are added to a solution of 2.1 g (0.12 mol) of ammonia gas and 2.04 g (0.03 mol) of sodium ethylate in 50 ml of ethanol at 5° C. and the mixture is boiled under reflux for 18 hours. The solvent is then distilled off in vacuo, the residue is dissolved in 60 ml of water and the mixture is brought to pH 4 by addition of concentrated hydrochloric acid and extracted 3 times with 50 ml of methylene chloride each time. The organic phases are dried over sodium sulphate and evaporated in vacuo.

3.6 g (86% of theory) of ethyl 6-hydroxy-3-pyridinecarboxylate are thus obtained in the form of beige crystals of melting point 143° C.-144° C.

Process variant (b))

A mixture of 0.75 g (0.011 mol) of sodium ethylate, 15 ml of methanol and 2.1 g (0.01 mol) of diethyl 1-amino-1,3-butadiene-2,4-dicarboxylate is boiled under reflux for 18 hours. The solvent is then distilled off in vacuo, the residue is dissolved in 20 ml of water and the solution is brought to pH 4 by addition of hydrochloric acid. It is extracted 3 times with 100 ml of methylene chloride each time, the organic phase is dried over sodium sulphate and the solvent is distilled off in vacuo.

1.4 g (84% of theory) of ethyl 6-hydroxy-3-pyridinecarboxylate of melting point 144° C. are obtained.

The following compounds of the formula (I) can be prepared analogously to Example 1 and the two process variants (a) and (b) described:

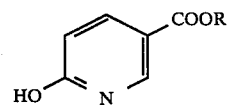 (I)

EXAMPLE 2

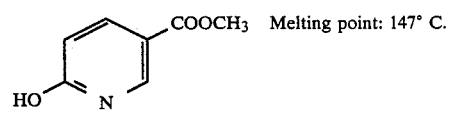 Melting point: 147° C.

EXAMPLE 3

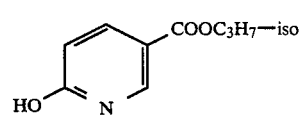

Starting compounds of the formula (II)

Example (II-1)

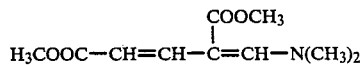

25.4 g (0.21 mol) of dimethylformamide dimethyl acetal are added dropwise to a mixture of 28 g (0.18 mol) of dimethyl glutaconate, 36.7 g (0.36 mol) of acetic anhydride and 200 ml of toluene. During this, the reaction mixture warms to about 27° C.; it is stirred for 18 hours without cooling and then evaporated at 50° C. in vacuo. The residue is freed from volatile constituents at 80° C. under a high vacuum.

30 g (78% of theory) of dimethyl 1-dimethylamino-1,3-butadiene-2,4-dicarboxylate are obtained in the form of beige crystals of melting point 62° C.

The following compounds of the formula (II) can be prepared analogously to Example (II-1):

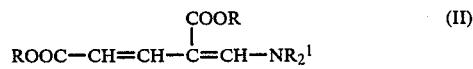 (II)

EXAMPLE (II-2)

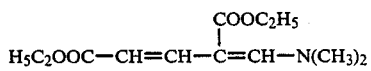

$n_D^{23}$:1.5715

EXAMPLE (II-3)

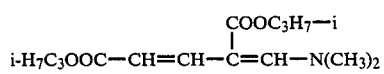

EXAMPLE (II-4)

Starting compounds of the formula (III)

EXAMPLE 4

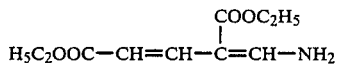

2.1 g (0.125 mol) of ammonia gas are dissolved in 50 ml of ethanol. 6 g (0.025 mol) of diethyl 1-dimethylamino-1,3-butadiene-2,4-dicarboxylate are added to this mixture and the reaction mixture is boiled under reflux for 24 hours. The solvent is then distilled off in vacuo, the residue is triturated with petroleum ether and the crystalline product is filtered off with suction.

4.5 g (84% of theory) of diethyl 1-amino-1,3-butadiene-2,4-dicarboxylate are obtained in the form of beige crystals of melting point 109° C.

The following compounds of the formula (III) can be prepared analogously to Example (III-1):

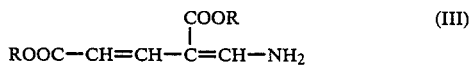 (III)

EXAMPLE (III-2)

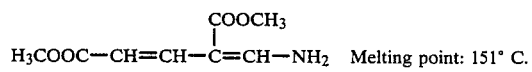 Melting point: 151° C.

EXAMPLE (III-3)

It will be understood that the specification and examples are illustrative but not limitative of the present invention and that other embodiments within the spirit and scope of the invention will suggest themselves to those skilled in the art.

I claim:

1. A process for the preparation of a 6-hydroxy-3-pyridinecarboxylic acid ester of the formula

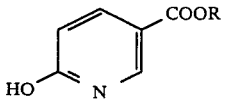

in which
R is alkyl,
comprising reacting a 1-dialkylamino-1,3-butadiene-2,4-dicarboxylic acid ester of the formula

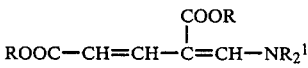

in which
$R^1$ is alkyl,
with
(a) gaseous ammonia in the presence of an alkali metal alcoholate and in the presence of a diluent at a temperature between 0° C. and 120°0 C., or
(b)
 (i) gaseous ammonia and in the presence of a diluent at a temperature between 0° C. and 50° C. in a first stage to give the amino derivative of the formula

and
 (ii) in a second stage reacting the amino derivative with an alkali metal alcoholate and in the presence of a diluent at a temperature between 0° and 120° C.

2. A process according to claim 1, in which R is $C_1$–$C_6$-alkyl.

3. A process according claim 1, wherein in (a) the reaction is carried out at 20° to 100° C.

4. A process according to claim 1, wherein in (a) 1 to 1.5 mols of alkali metal alcoholate and 2 to 10 mols of gaseous ammonia are employed per mol of the 1-dialkylamino-1,3-butadiene-2,4-dicarboxylic acid ester.

5. A process according to claim 1, wherein in (a) an aromatic hydrocarbon is used as the diluent.

6. A process according to claim 1, wherein (b) (i) is carried out at 10° to 35° C., and (b) (ii) is carried out at 20° to 100° C.

7. A process according to claim 1, wherein in (b) (i) 2 to 10 mols of gaseous ammonia are used per mol of the 1-dialkylamino-1,3-butadiene-2,4-dicarboxylic acid ester and in (b) (ii) 1 to 1.5 mols of alcoholate are used per mol of the amino derivative.

8. A process according to claim 1, wherein in (b) (i) and (ii) a lower alcohol is used as the diluent.

* * * * *